United States Patent
Coelho

(12) 
(10) Patent No.: US 6,251,084 B1
(45) Date of Patent: Jun. 26, 2001

(54) GUIDE CATHETER AND GUIDEWIRES FOR EFFECTING RAPID CATHETER EXCHANGE

(75) Inventor: Donald A. Coelho, Wakefield, MA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 07/863,154

(22) Filed: Apr. 2, 1992

Related U.S. Application Data

(63) Continuation of application No. 07/391,419, filed on Aug. 9, 1989, now abandoned.

(51) Int. Cl.[7] .................................................. A61M 25/00
(52) U.S. Cl. ...................... 600/585; 606/194; 604/103.04
(58) Field of Search ............................... 604/53, 96–103, 604/165, 169, 170, 280, 103.04; 606/194; 128/657, 658, 772; 600/585

(56) References Cited

U.S. PATENT DOCUMENTS

| | | | |
|---|---|---|---|
| 2,819,718 | * 1/1958 | Goldman | 604/96 |
| 2,919,697 | * 1/1960 | Kim | 604/102 |
| 3,983,879 | 10/1976 | Todd . | |
| 3,996,938 | 12/1976 | Clark, III . | |
| 4,166,468 | * 9/1979 | Haynie | 604/256 |
| 4,285,341 | * 8/1981 | Pollack | 604/99 |
| 4,364,394 | * 12/1982 | Wilkinson | 604/96 |
| 4,582,181 | * 4/1986 | Samson | 606/194 |
| 4,606,347 | * 8/1986 | Fogarty et al. | 606/194 |
| 4,771,777 | * 9/1988 | Horzewski et al. | 604/101 |
| 4,779,628 | 10/1988 | Machek | 128/772 |
| 4,781,682 | 11/1988 | Patel | 604/96 |
| 4,787,399 | * 11/1988 | Bonello | 604/95 |
| 4,798,193 | 1/1989 | Giesy et al. | 128/7 |
| 4,827,941 | * 5/1989 | Taylor et al. | 128/772 |
| 4,832,028 | * 5/1989 | Patel | 606/194 |
| 4,844,092 | 7/1989 | Rydell et al. | 128/772 |
| 4,932,959 | * 6/1990 | Horzewski et al. | 606/194 |
| 4,947,864 | * 8/1990 | Shockey et al. | 128/657 |
| 4,988,356 | * 1/1991 | Crittenden et al. | 606/192 |

FOREIGN PATENT DOCUMENTS

| | | |
|---|---|---|
| 0244955 | 11/1987 | (EP) . |
| WO8801885 | 3/1988 | (WO) . |

* cited by examiner

Primary Examiner—Ralph A. Lewis
(74) Attorney, Agent, or Firm—Sterne, Kessler, Goldstein & Fox PLLC

(57) ABSTRACT

A system and method for effecting rapid exchange of catheters over a guidewire. A gripping mechanism is provided on one of a guide catheter and a guidewire to grip the other of the guide catheter and guidewire proximate to the distal end of the guide catheter. When engaged, the gripping mechanism inhibits movement between the guidewire and the guide catheter when a first catheter is exchanged with a second catheter over the guidewire.

5 Claims, 2 Drawing Sheets

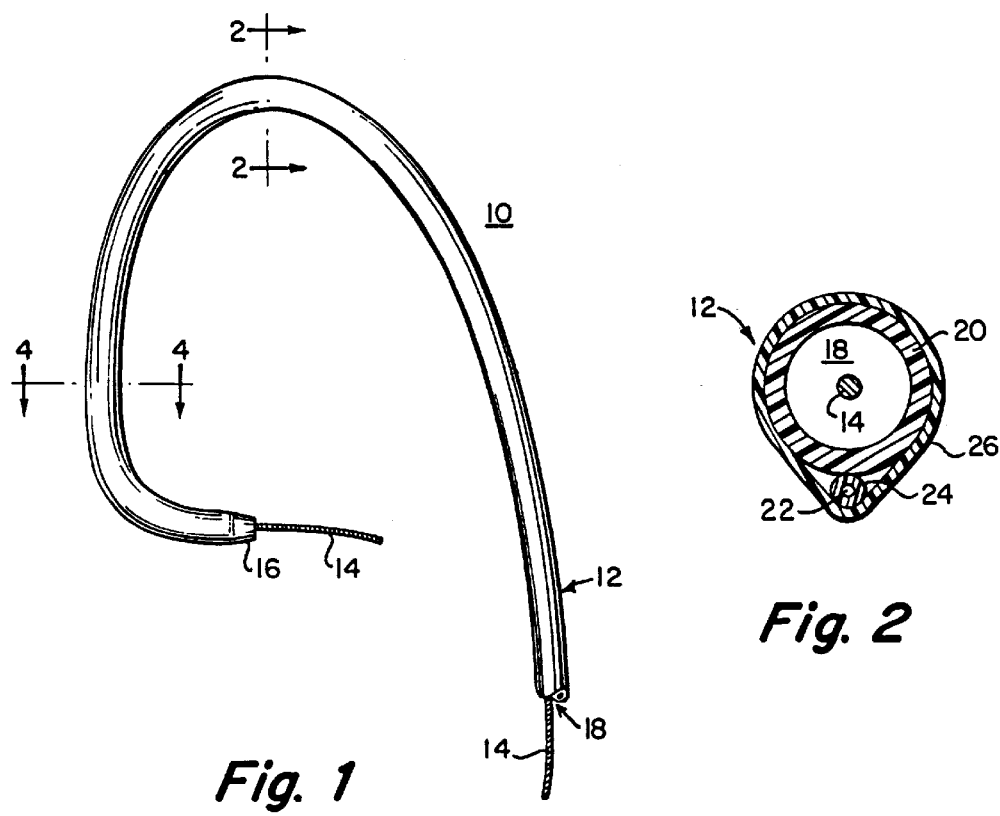
Fig. 1
Fig. 2
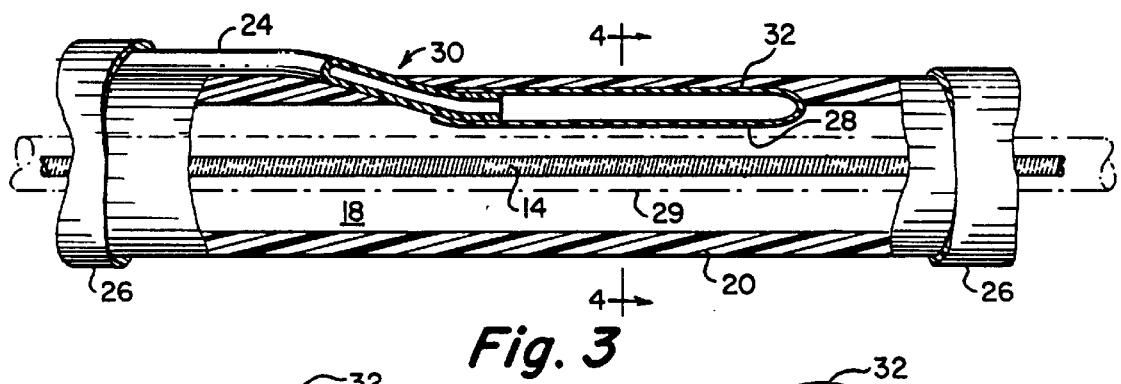
Fig. 3
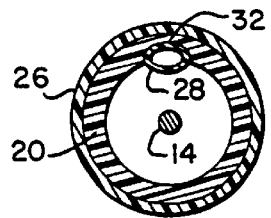
Fig. 4A
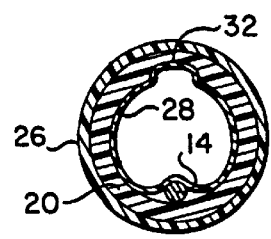
Fig. 4B

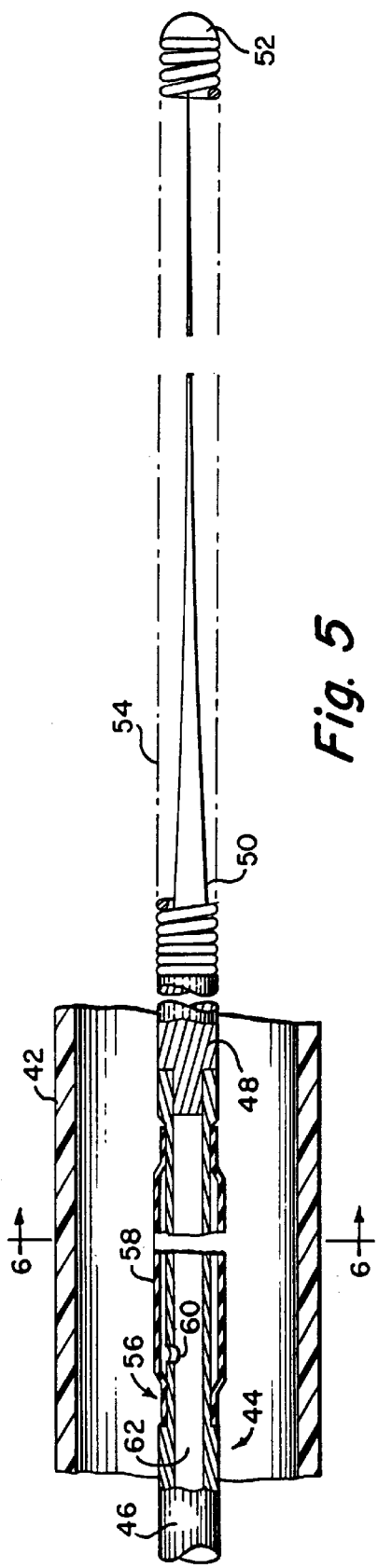
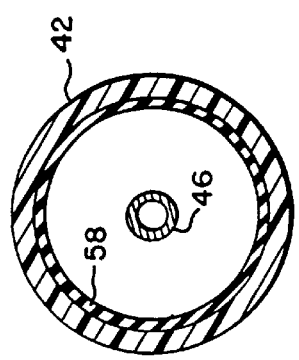
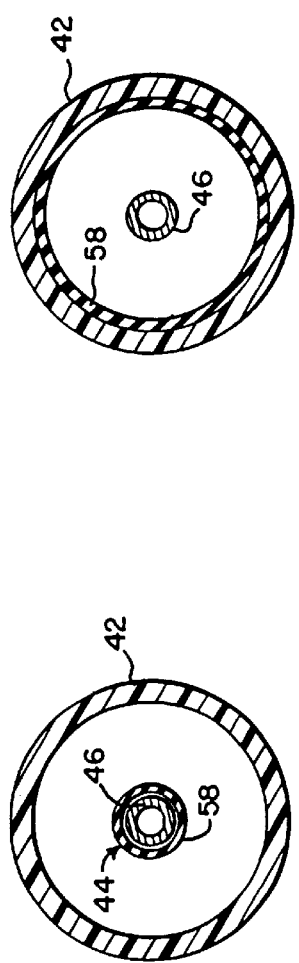
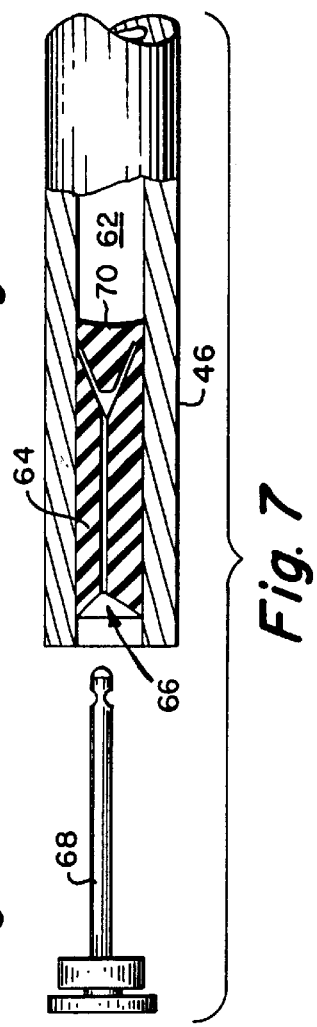

GUIDE CATHETER AND GUIDEWIRES FOR EFFECTING RAPID CATHETER EXCHANGE

This application is a continuation of application Ser. No. 07/391,419 filed Aug. 9, 1989 now abandoned.

FIELD OF THE INVENTION

This invention relates to guidewires and guide catheters used in vascular catheterization procedures, and to techniques for performing catheter exchanges.

BACKGROUND OF THE INVENTION

In vascular catheterization procedures it often is necessary for a physician to use different catheters in the diagnosis or treatment of a particular blood vessel. For example, when performing percutaneus transluminal coronary angioplasty (PTCA), a physician commonly will use a series of dilatation catheters to be inserted into the patient. Each of the catheters has a different shape, size, or configuration suited for a specific purpose.

Dilatation catheters, and particularly those used for PTCA, typically include an elongate flexible shaft of the order of 150 cm long having a dilatation balloon mounted to the distal end of the shaft and an inflation lumen extending longitudinally within the shaft from its proximal end to the interior of the balloon so that the balloon may be inflated and deflated. Typically, such PTCA catheters also are provided with a full length guidewire lumen that is open at the distal tip of the shaft at a distal outlet opening. The proximal end of the guidewire lumen is open at the proximal end of the catheter. The guidewire lumen receives a guidewire which, when the guidewire and catheter are placed within a patient's artery, can be manipulated to guide the wire and catheter to the desired branch of the patient's arteries.

Typically, the balloon dilatation catheter and guidewire are guided to the entrance to the coronary arteries by a previously placed guide catheter. The guide catheter commonly is percutaneously inserted into the patient's femoral artery and is advanced along the aorta toward the heart. The guide catheter typically is provided with a preshaped distal tip adapted to remain at the coronary ostium leading to the coronary artery. Once placed, the guide catheter provides direct, quick access to the entrance to the coronary arteries.

It is common during a PTCA procedure for the physician to exchange the balloon catheter for another catheter, for example, if it is desired to change balloon sizes. This may occur, for example, if the physician initially performed a partial dilatation with a small diameter balloon and then wished to further dilate the patient's artery by using a catheter having a larger balloon. Treatment of multiple lesions in an artery often requires three or more different balloon sizes. Each change in balloon size requires a catheter exchange.

Such a catheter exchange may be accomplished in several ways. In one technique, the conventional guidewire which may be approximately 175 cm long is removed from the in situ balloon catheter and is replaced with a longer exchange wire, typically about 300 cm long. The length of the exchange wire that extends out of the patient is greater than the length of the balloon catheter thus providing a means by which the guidewire may be grasped at all times to prevent inadvertent withdrawal of the guidewire as the catheter is withdrawn. Once the catheter is withdrawn over the exchange wire, the next catheter can be threaded over the exchange wire and inserted into the patient, the exchange wire providing a direct path to guide the catheter to the portion of the artery to be dilated. If desired, the exchange wire then may be removed and replaced with a shorter conventional wire, although some physicians may prefer to permit the exchange wire to remain in place for the remainder of the procedure.

Another technique omits the necessity for an exchange wire by providing a guidewire extension that is attached to the proximal end of the guidewire thereby effectively extending the length of the guidewire that protrudes out of a patient sufficiently to permit the catheter to be withdrawn and a new catheter to be threaded back into the patient without losing guidewire position.

Still another technique for performing a catheter exchange is that described in "New Instruments for Catheterization and Angiocardiography" by Bjorn Nordenstrom, *Radiology*, Vol. 85, 1965, pp. 256–259, which describes a catheter having a relatively short guidewire lumen at the distal end of the catheter, the guidewire lumen having a proximal terminal opening located distally of the proximal end of the catheter shaft. In this arrangement, the guidewire passes through the catheter shaft only for a segment of the length of the shaft. The catheter can be moved along the guidewire in the fashion of a "monorail". Because the guidewire lumen is relatively short and is considerably shorter than the overall length of the catheter, the catheter can be withdrawn from the patient over the original guidewire without dragging the guidewire out of the artery together with the catheter because the length of guidewire protruding from the patient is longer than the length of the guidewire lumen of the catheter. Thus, a portion of the guidewire is exposed at all times and may be grasped by the physician. Such a monorail system has recently been incorporated into PTCA catheters as illustrated, for example, in U.S. Pat. Nos. 4,762,129 (Bonzel) and 4,748,982 (Horzewski).

Although the use of the monorail system facilitates catheter exchanges, the PTCA catheters in which the monorail system have been incorporated have presented some difficulties. One of the problems presented is that because the guidewire only extends through a relatively small portion of the overall length of the catheter, the remaining portion of the catheter shaft is unsupported by the guidewire. When the balloon catheter and guidewire are advanced through the guide catheter by pushing the catheter shaft, the unsupported portion of the catheter shaft tends to buckle within the guide catheter. Buckling of the catheter shaft within the guide catheter increases the number and area of points of contact between the catheter shaft and the inner surface of the guide catheter lumen, thus increasing friction and causing the balloon catheter to bind up in the guide catheter and impairing the ability of the catheter to be pushed along the guidewire. The tendency to become bound up in the guide catheter increases with the extent to which the catheter is advanced through the guide catheter and prevents the catheter from being advanced into distal coronary vasculature. The tendency for the dilatation catheter shaft to buckle is particularly acute in the region of the aortic arch.

Additional difficulties presented by the monorail system include the inability to exchange guidewires after the monorail catheter is inserted into the guide catheter. For example, if a physician decides that a more flexible guidewire is required, a monorail catheter must be fully withdrawn to access the proximal end of its short guidewire lumen. Moreover, once withdrawn, the catheter cannot direct the new guidewire to the previously achieved position within the coronary artery; the guidewire must be steered anew beyond the distal end of the guide catheter.

Another disadvantage is that a monorail catheter cannot be exchanged with a conventional dilatation catheter having a full-length guidewire lumen unless an exchange wire is utilized. Further, the shortened guidewire lumen of a monorail catheter requires a separate, full-length lumen for measurement of pressure or injection of dye or other fluids. It is desirable to use the guidewire lumen to accomplish such fluid introductions or pressure measurements to eliminate the need to provide an extra lumen. The provision of an extra lumen must increase the overall outer diameter of the dilatation catheter which may prevent its use in smaller arteries.

It is among the general objects of the invention to provide an improved guide catheter and guidewire system having a rapid exchange feature which avoids the foregoing and other difficulties.

SUMMARY OF THE INVENTION

The present invention enables a catheter exchange to be made without requiring any guidewire exchanges and without the problems of the monorail system. In accordance with the present invention a mechanism is provided on one of a guide catheter and a guidewire to selectively grip the other of the guide catheter and the guidewire. When engaged, the mechanism inhibits movement between the guide catheter and the guidewire when a first catheter is exchanged with a second catheter over the guidewire. Therefore, it is not necessary to extend the length of the guidewire or to substitute it for an exchange wire. Instead, the original guidewire remains in place during the entire catheter exchange. Use of the mechanism substantially shortens the duration of the procedure because an entire additional step is eliminated. Additionally, there is a further reduction in the risk of puncturing the blood vessel. There is also less exposure to fluoroscopic radiation which is required each time a guidewire is inserted.

In one embodiment, the mechanism is an inflatable balloon disposed on the guide catheter proximate to its distal end. When inflated, the balloon frictionally grips a guidewire to immobilize it. Preferably, the balloon is formed of a elastic material and extends along a portion of the inside of the guide catheter. The guide catheter includes an inflation/deflation lumen having a proximal end and a distal end communicating with the balloon, the lumen being defined by tubing which extends along the outside surface of the guide catheter and enters through a port defined by the guide catheter. An outer jacket surrounds the tubing and the guide catheter to provide an integral device. The guide catheter may define a longitudinal recess in the interior surface for receiving a balloon when it is deflated.

In another embodiment, the mechanism is an inflatable balloon disposed on a guidewire. Preferably, the balloon is formed of a elastic material and is disposed about the outside surface of a section of the guidewire. The guidewire defines an inflation/deflation lumen which communicates with the balloon through a port in a section of the guidewire. A substantial portion of he guidewire may be a hollow tube which defines the inflation/deflation lumen. The tube may be a hollow metal tube which is sealed at its distal end by the proximal end of a metal core wire. A spring coil extends distally from the sealed hollow tube and the core wire extends within the spring coil. The spring coil provides a section of greater flexibility at the distal end of the guidewire to enhance movement of the guidewire through an artery.

Preferably, the guidewire further includes a valve disposed within the proximal end of the inflation/deflation lumen. Fluid is introduced under pressure through the valve to inflate the balloon and the valve maintains the balloon in an inflated, pressurized condition during catheter exchange. Because the valve is disposed within the guidewire, each catheter can be advanced or withdrawn over the proximal end of the guidewire without disrupting balloon inflation which interlocks the guidewire with the guide catheter.

The balloon may be disposed on the guidewire at least 10 cm, and preferably 20–40 cm, proximally of the distal end of the guidewire. A preferred elastic material for the balloon is latex. Although it is preferred to use an elastic material, other flexible less elastic materials such as vinyl may be used.

It is among the objects of the invention provide a new and improved technique for performing catheter exchanges.

Another object of the invention is to provide an improved guidewire which enables catheter exchanges to be performed without the use of an exchange wire or monorail catheters.

It is a further object of the invention to provide such an improved guidewire which can be used with a standard guide catheter.

A further object of the invention is to provide an improved catheter which enables catheter exchanges to be performed without the use of an exchange wire.

A still further object of the invention is to provide such an improved guide catheter which can be used with a standard guidewire.

Another object of the invention is to provide a technique for performing catheter exchange which is quick and reduces the amount of fluoroscopic exposure.

A still further object of the invention is to provide method and apparatus for engaging the guide catheter and the guidewire to each other while the guidewire is in place to facilitate catheter exchanges over the immobilized guidewire.

Another object of the invention is to provide a system of the type described in which the guide catheter can be disengaged from the guidewire after the catheter exchange has been completed.

Yet another object of the invention is to provide such a system which accommodates standard intracoronry catheters and obviates any need to modify catheters.

BRIEF DESCRIPTION OF THE DRAWINGS

FIG. 1 is a schematic perspective drawing of the distal portions of a guide catheter and guidewire of the invention;

FIG. 2 is a cross-sectional view along lines 2—2

FIG. 3 is a schematic of a partial longitudinal section of a portion at the distal end of the guide catheter and the guidewire showing a gripping balloon according to the invention disposed on the guide catheter;

FIGS. 4A and 4B are cross-sectional views along lines 4—4 of FIG. 1 before and after inflation of the gripping balloon;

FIG. 5 is a schematic cross-sectional representation of another preferred embodiment of the invention showing a gripping balloon carried by the guidewire;

FIGS. 6A and 6B are schematic cross-sectional views along lines 6—6 of FIG. 5 before and after balloon inflation; and FIG. 7 is a schematic cross-sectional representation of the proximal end of the guidewire showing a valve disposed in the inflation/deflation lumen and an inflation needle insertable within the valve.

DETAILED DESCRIPTION OF THE DRAWINGS

The invention can be accomplished by a guide catheter and a guidewire, one of which carries a mechanism for gripping the other during exchange of a first catheter for a second catheter over the guidewire. System 10 according to the invention, FIG. 1, includes a guide catheter assembly 12 having an inflatable gripping balloon and a conventional guidewire 14 which is extendable beyond the distal end 16 of the guide catheter assembly 12. The guidewire 14 passes through a lumen 18 defined by guide catheter 20 of the guide catheter assembly 12, as shown in cross-section in FIG. 2. In this construction the gripping mechanism is an inflatable balloon which is inflated and deflated through a lumen 22 defined by a tube 24. The guide catheter 20 and the tube 24 are joined as an integral unit by a jacket 26. The guide catheter assembly 12 is shaped to direct the guidewire 14 into a coronary artery.

The inflatable balloon 28 for gripping the guidewire 14 is disposed near the distal end 16 of the guide catheter assembly 12 as shown in FIG. 3. The tube 24 passes through port 30 in the guide catheter 20 to communicate with the gripping balloon 28. Preferably, a longitudinal recess 32 is provided in the interior surface of the guide catheter 20 to receive the gripping balloon 28 in the deflated condition, as also shown in FIG. 4A.

During use of the exchange system according to the invention, the guide catheter assembly 12 is inserted through a selected blood vessel until the distal end 16 is positioned within the aorta. The guidewire 14, alone or together with a first catheter such as a balloon dilatation catheter, is then inserted through the lumen 18 until it emerges from the distal end 16. The guidewire is then steered to a selected location in a coronary artery. The balloon catheter is advanced over the guidewire 14 and through the lumen 18 until the dilatation balloon is positioned at a stenosis to be treated. A portion of a dilatation catheter 29 is shown in phantom in FIG. 3; the illustrated sizes of the catheter 29, the guide catheter 20 and the guidewire 14 are not to scale. The dilatation balloon is inflated to dilate the stenosis, after which the dilatation balloon is deflated and the balloon catheter withdrawn. During withdrawal of the balloon catheter, the proximal end of the guidewire 14 is held by an operator until the distal end of the dilatation catheter is proximal to the gripping balloon 28. An inflation device such as a syringe is connected to a luer communicating with the proximal end of the inflation lumen 22 to actuate the gripping mechanism. The gripping balloon 28 inflates and traps the guidewire 14 against the opposite wall of the lumen 18 as shown in FIG. 4B. The frictional grip between the balloon 28 and the guidewire 14 immobilizes the guidewire 14 to enable the balloon catheter to be fully removed. A second catheter is then inserted over the proximal end of the guidewire 14 and advanced until its distal end reaches the inflated gripping balloon 28. The balloon 28 is then evacuated to return it to the deflated condition shown in FIG. 4A. Because the guidewire 14 is selected to have a length which is also greater than that of the second balloon catheter, the operator can again access the proximal end of the guidewire 14 to grasp it while the second catheter is advanced distally along the guidewire 14 beyond the deflated gripping balloon 28 to perform the next desired treatment. This technique eliminates the need to use a separate exchange wire, thus saving time and reducing the risk of injury to the arterial walls. Further, exchange is accomplished without using a monorail system with its attendant disadvantages.

In one construction, the guide catheter 20 is similar in size to the large lumen 8F catheter, FL4DX, catalog no. 004743, available from USCI, a division of C. R. Bard, Inc. The catheter 20 has an overall usable length of approximately 100 cm, a minimal inner diameter of 0.076 inch and a minimal outer diameter of 0.105 inch. Urethane is an acceptable material for the guide catheter 20 and polyurethane or heat-shrink tubing is acceptable for the outer jacket 26. The inflation tube 24 is a polyimide tube having an inner diameter of 0.012 inch and an outer diameter of 0.014 inch and runs the full length of the guide catheter from a proximal luer to the port 30 which is 0.015 inch in diameter and angled at approximately 30–45°. The gripping balloon 28 is bonded to the polyimide tube 24 and overlaps it by 1–2 mm. Latex is a suitable material for the gripping balloon 28 because it has a relatively high coefficient of friction and is elastic. The gripping balloon 28 is positioned approximately 3 cm from the distal end 16. At atmospheric pressure, the balloon has an inner diameter of 0.010 inch, a wall thickness of 0.0035–0.004 inch and an overall length of 10 mm. Although the balloon 24 is shown as having a smooth outer surface, the balloon may be provided with annular ribs separated by annular thin sections which differentially expand during inflation to provide a non-uniform surface to preferentially grip the external surface of the guidewire 14. The balloon can be inflated using an inflation device such as the Wizard, available from USCI, catalog no. 006296. A wide range of standard guidewires may be used as the guidewire 14, typically having an outer diameter ranging from 0.014–0.018 inch for PTCA.

During manufacture of the above guide catheter assembly, the gripping balloon 28 is attached to the distal end of the tubing 24 and is introduced into lumen 18 through the port 30. The balloon 28 is preferably tacked in place within the recess 32 by an adhesive. The recess 32 is formed during fabrication of the guide catheter 20 by casting it about a mandrel having a longitudinal projection. In an embodiment in which a longitudinal recess 32 is not present, the gripping balloon 28 may be attached by adhesive in one or more places to the inner surface of the guide catheter 20.

Instead of the inflation lumen being formed by a separate tube, a lumen can be provided in the guide catheter itself. The balloon may be a "patch" in which all four edges of the material are bonded to the interior surface of the catheter over a port which communicates with the inner lumen. Alternatively, a tubular balloon having a sealed distal end and an open proximal end may be used, in which the open proximal end is bonded about the port. In yet another embodiment, a metal bar can be actuated to slide down an angled groove to pinch the guidewire against the inner surface of the guide catheter, or a retractable loop can be established to form a snare which is collapsible upon the guidewire. A still further embodiment utilizes a laminated braid or mesh which can be actuated to collapse upon the guidewire to immobilize it relative to the guide catheter. In all of these embodiments it is desirable for the gripping mechanism to be repeatedly usable to alternatively grip and release the guidewire and to accommodate the passage of successive catheters over the guidewire.

In another embodiment of the invention, the gripping mechanism is disposed on the guidewire which is used with a conventional guide catheter. The system 40 according to the invention, FIG. 5, includes conventional guide catheter 42 and guidewire assembly 44. The proximal portion of the guidewire 44 is formed of a stainless steel hollow tube 46 which is brazed at its distal end to metal plug 48. In this construction, plug 48 is the proximal end of a stainless steel core wire 50 which extends to distal tip bead 52. The proximal end of the core wire 50 is ground to form a neck which is inserted within the distal end of the tube 46 and then brazed. An outer spring coil 54 having closely packed coils extends from the plug 48 to the tip bead 52. This arrangement provides a distal portion which is more flexible than the proximal portion of the guidewire assembly 44, particularly when the core wire 50 is tapered toward the distal end. The more flexible distal portion reduces risk to arterial walls and aids placement of the guidewire. The balloon 58 remains within the guide catheter 42 at all times.

An annular recess 56 is provided near the distal end of the tube 46 to accommodate a gripping balloon 58 which is bonded at its distal and proximal ends to the tube 46. A port 60 connects lumen 62 defined by hollow tube 46 with the interior of the gripping balloon 58. The balloon 58 is shown in the deflated condition in FIG. 6A in which standard catheters can be advanced and retracted over the guidewire assembly 44. After a first catheter to be exchanged has been removed proximal to the balloon 58, pressurized fluid is introduced through tube 46 to inflate balloon 58 to grip the interior surface of the conventional guide catheter 42 as shown in FIG. 6B.

The technique of exchanging catheters is similar to that described above in relation to FIGS. 4A–4B, except that an inflation device cannot remain connected to the guidewire while the catheters are removed and inserted over the proximal end of the guidewire assembly 44. To maintain the gripping balloon in an inflated condition, the proximal end of the tube 46 is provided with a valve 64, FIG. 7, which defines passage 66 through which needle 68 is inserted to inflate the balloon. After pin 68 is withdrawn, the higher pressure inside lumen 62 drives cone 70 against the distal opening of the passage 66, thereby automatically sealing the lumen 62. Catheters can thereby be passed over the proximal end of the tube 46 while the gripping balloon is maintained in the inflated condition. The gripping balloon 58 is deflated when desired by reinserting the pin 68 and drawing a vacuum to evacuate the lumen 62.

In one construction, the guidewire assembly 44 is 180 cm in length and contains one or more radiopaque segments, one of which is disposed near the gripping balloon 58 to enable a physician to confirm through fluoroscopy that the gripping balloon is properly positioned within the interior of the guide catheter. The tube 46 is approximately 150 cm in length having an outer diameter of 0.018 inch and an inner diameter of 0.014 inch. The automatically sealing valve 64 is formed of silicone rubber and is approximately 5 mm in length.

The inflation port 60 is formed approximately 2 cm from the distal end of the tube 46. The gripping balloon 58 is formed of a elastic latex material and when relaxed has an inner diameter of 0.014 inch and a wall thickness of 0.003 inch. The gripping balloon 58 inflates to an outer diameter at least as large as the inner diameter of the guide catheter, in this case approximately 0.08 inch. The gripping balloon 58 is approximately 10 mm in length and is therefore disposed approximately 31 cm proximal to the distal tip 52 of the guidewire assembly 44. It is desirable for the gripping balloon 58 to be disposed at least 10 cm and preferably 20–40 cm proximal to the distal tip bead 52 to accommodate a more flexible distal section which need not define an inflation lumen.

Instead of an inflatable balloon, the gripping mechanism can be another selectively expandable element such that, when disposed on the guidewire, the gripping mechanism enables rapid catheter exchange when used in combination with a wide variety of conventional guide catheters. Conversely, as described above, a gripping mechanism disposed in the guide catheter enables a rapid exchange system in which a large number of standard guidewires can be used. Although described in relation to coronary angioplasty, an exchange system according to the invention can be used for any technique which uses a guide catheter and a guidewire in a body lumen.

Various changes and modifications to the embodiments shown in the drawings and described above may be made within the scope of the invention. Therefore, it is intended that all matter contained in the above description and shown in the accompanying drawings shall be interpreted in an illustrative and not limited sense.

What is claimed is:

1. A method of exchanging a first catheter with a second catheter through a guide catheter indwelling in a living human, the first catheter having been inserted into the indwelling guide catheter over a guidewire, at least one of the first and second catheters having a guidewire lumen extending the full length thereof, the method comprising the steps of:

providing a mechanism to inhibit movement of the guidewire relative to the guide catheter;

operating the mechanism to inhibit said relative movement; and exchanging said first and second catheters, while said relative movement is inhibited by the mechanism, by withdrawing the first catheter from the indwelling guide catheter, separating the first catheter completely from the guidewire, and then inserting the second catheter into the indwelling guide catheter over the guidewire.

2. A method of exchanging a first catheter with a second catheter, the first catheter being inserted over a guidewire and extending through a guide catheter with a body lumen, comprising:

withdrawing the distal end of the first catheter proximal to the distal end of the guide catheter, the first catheter remaining substantially within said guide catheter;

inflating a balloon disposed on the guide catheter to grip the guidewire to inhibit movement of the guide catheter and guidewire relative to each other;

fully withdrawing the first catheter over the guidewire;

inserting the second catheter over the guidewire and advancing it up to the Balloon;

deflating the balloon to disengage the guide catheter and the guidewire relative to each other; and fully advancing the second catheter distal to the distal end of the guide catheter.

3. A method for exchanging a first over-the-wire catheter on a guide wire in a patient's vascular system for a second over-the-wire catheter on the guide wire, wherein the guide wire extends through and past a distal end of a guide catheter, the method comprising the steps of:

providing an inflatable wire-captivation balloon within the guide catheter;

holding a proximal end of the guide wire outside of the vascular system to maintain position of the guide wire longitudinally relative to the guide catheter and the vascular system;

moving the first over-the-wire catheter on the guide wire into the guide catheter to a position proximal of the wire-captivation balloon;

inflating the wire-captivation balloon to a size such that movement of the guide wire longitudinally relative to the guide catheter is limited;

releasing the proximal end of the guide wire;

withdrawing the first over-the-wire catheter from a proximal end of the guide wire;

installing the second over-the-wire catheter onto the proximal end of the guide wire;

moving the second over-the-wire catheter to a position just proximal of the inflated wire-captivation balloon;

holding the proximal end of the guide wire outside of the vascular system to maintain position of the guide wire longitudinally relative to the guide catheter and the vascular system;

deflating the wire-captivation balloon to release the guide wire from its fixed position relative to the guide catheter; and moving the second over-the-wire catheter distally of the wire-captivation balloon.

4. A method of exchanging a first catheter with a second catheter, the first catheter being inserted over a guidewire and extending through a guide catheter within a body lumen, comprising:

withdrawing the distal end of the first catheter proximal to the distal end of the guide catheter, the first catheter remaining substantially within said guide catheter;

actuating a mechanism disposed on one of the guide catheter and the guidewire to frictionally engage the other of the guide catheter and the guidewire to inhibit movement of the guide catheter and guidewire relative to each other;

fully withdrawing the first catheter over the guidewire;

inserting the second catheter over the guidewire and advancing it up to the mechanism;

actuating the mechanism to disengage the guide catheter and the guidewire relative to each other; and fully advancing the second catheter distal to the distal end of the guide catheter to effect catheter exchange without requiring removal of the guidewire.

5. A method of exchanging a first catheter with a second catheter, the first catheter being inserted over a guidewire and extending through a guide catheter with a body lumen, comprising:

withdrawing the distal end of the first catheter proximal to the distal end of the guide catheter, the first catheter remaining substantially within said guide catheter;

inflating a balloon disposed on the guidewire to grip the guide catheter to inhibit movement of the guide catheter and guidewire relative to each other;

fully withdrawing the first catheter over the guidewire;

inserting the second catheter over the guidewire and advancing it up to the Balloon;

deflating the balloon to disengage the guide catheter and the guidewire relative to each other; and fully advancing the second catheter distal to the distal end of the guide catheter.

* * * * *